United States Patent
Novosad et al.

(10) Patent No.: US 12,290,705 B2
(45) Date of Patent: May 6, 2025

(54) REAL-TIME MOTION MONITORING USING DEEP LEARNING

(71) Applicant: Elekta Limited, Montreal (CA)

(72) Inventors: Philip P. Novosad, Montreal (CA); Silvain Beriault, Longueuil (CA)

(73) Assignee: Elekta Limited, Montreal (CA)

( * ) Notice: Subject to any disclaimer, the term of this patent is extended or adjusted under 35 U.S.C. 154(b) by 418 days.

(21) Appl. No.: 17/906,417

(22) PCT Filed: Mar. 10, 2021

(86) PCT No.: PCT/CA2021/050316
§ 371 (c)(1),
(2) Date: Sep. 15, 2022

(87) PCT Pub. No.: WO2021/184107
PCT Pub. Date: Sep. 23, 2021

(65) Prior Publication Data
US 2023/0126640 A1    Apr. 27, 2023

Related U.S. Application Data

(60) Provisional application No. 62/991,356, filed on Mar. 18, 2020.

(51) Int. Cl.
*G06K 9/00* (2022.01)
*A61N 5/10* (2006.01)
(Continued)

(52) U.S. Cl.
CPC .......... *A61N 5/1049* (2013.01); *G06T 7/0016* (2013.01); *G06T 7/262* (2017.01);
(Continued)

(58) Field of Classification Search
CPC .......... A61N 5/1049; A61N 2005/1055; A61N 2005/1061; A61N 5/1037;
(Continued)

(56) References Cited

U.S. PATENT DOCUMENTS

| | | | |
|---|---|---|---|
| 10,350,434 B2 * | 7/2019 | Rapaka | G06T 7/73 |
| 10,565,707 B2 * | 2/2020 | Liu | G06T 7/0012 |

(Continued)

FOREIGN PATENT DOCUMENTS

| | | |
|---|---|---|
| WO | WO-2019183584 A1 | 9/2019 |
| WO | WO-2021184107 A1 | 9/2021 |

OTHER PUBLICATIONS

"International Application Serial No. PCT/CA2021/050316, PCT Search Report mailed May 20, 2021", 3 pgs.

(Continued)

*Primary Examiner* — Shervin K Nakhjavan
(74) *Attorney, Agent, or Firm* — Schwegman Lundberg & Woessner, P.A.

(57) ABSTRACT

Systems and methods may be used for estimating instantaneous patient motion (a patient state). The patient state may be estimated based on a 3D reference volume and a stream of images, for example from an image acquisition device. The stream of images may be received in real-time, for example during a radiation therapy treatment. An example method may include encoding the 3D reference volume using a 3D encoder branch of a patient state generator network, encoding the stream of images using a 2D encoder branch of the patient state generator network, and combining the encoded 3D reference volume and the encoded real-time stream of images. The method may include estimating a 3D spatial transform that maps the 3D reference volume to a current patient state by decoding the combined encoding using a 3D decoder branch of the patient state generator network.

20 Claims, 8 Drawing Sheets

(51) Int. Cl.
*G06T 7/00* (2017.01)
*G06T 7/262* (2017.01)

(52) U.S. Cl.
CPC .......... *A61N 2005/1055* (2013.01); *A61N 2005/1061* (2013.01); *G06T 2207/10016* (2013.01); *G06T 2207/10081* (2013.01); *G06T 2207/10088* (2013.01); *G06T 2207/20081* (2013.01); *G06T 2207/20084* (2013.01); *G06T 2207/30004* (2013.01)

(58) Field of Classification Search
CPC .......... A61N 2005/1054; G06T 7/0016; G06T 7/262; G06T 2207/10016; G06T 2207/10081; G06T 2207/10088; G06T 2207/20081; G06T 2207/20084; G06T 2207/30004; G06T 7/30; G06T 7/70; G06T 2207/10072; G06T 2207/10116; G06T 2207/10132; G06N 3/045; G06N 3/08; A61B 6/037; A61B 5/7207; A61B 6/032; A61B 6/5211; A61B 5/7267; A61B 2576/00; A61B 5/055; G16H 30/40; G16H 50/20
See application file for complete search history.

(56) References Cited

U.S. PATENT DOCUMENTS

| | | | | |
|---|---|---|---|---|
| 10,753,997 | B2* | 8/2020 | Odry | G01R 33/543 |
| 10,762,398 | B2* | 9/2020 | Sjölund | G06V 10/454 |
| 10,818,019 | B2* | 10/2020 | Piat | G06T 15/08 |
| 11,158,069 | B2* | 10/2021 | Shi | G06T 7/30 |
| 11,348,227 | B2* | 5/2022 | Fan | G06V 10/25 |
| 11,623,106 | B2* | 4/2023 | Haas | A61N 5/1037 |
| | | | | 378/65 |
| 11,756,160 | B2* | 9/2023 | Park | G06N 3/048 |
| | | | | 382/276 |
| 12,016,717 | B2* | 6/2024 | Guo | A61B 6/466 |
| 12,033,247 | B2* | 7/2024 | Balashova | G06N 20/00 |
| 12,045,993 | B2* | 7/2024 | Novosad | A61N 5/1039 |
| 12,067,725 | B2* | 8/2024 | Wang | A61B 5/055 |
| 12,164,014 | B2* | 12/2024 | Lee | G01R 33/56518 |
| 2016/0114192 | A1* | 4/2016 | Lachaine | A61N 5/1037 |
| | | | | 600/1 |
| 2017/0337682 | A1* | 11/2017 | Liao | G06T 7/30 |
| 2017/0360325 | A1 | 12/2017 | Hebert | |
| 2019/0154785 | A1 | 5/2019 | Zhou et al. | |
| 2019/0287682 | A1 | 9/2019 | van Zon et al. | |
| 2019/0311202 | A1* | 10/2019 | Lee | G06T 9/002 |
| 2020/0020098 | A1* | 1/2020 | Odry | G06T 7/0012 |
| 2022/0245933 | A1* | 8/2022 | Zhao | G06N 3/08 |
| 2023/0129194 | A1* | 4/2023 | Vazquez Romaguera | G06T 7/0012 |
| | | | | 378/65 |
| 2024/0394883 | A1* | 11/2024 | Liao | G06T 7/0012 |

OTHER PUBLICATIONS

"International Application Serial No. PCT/CA2021/050316, Written Opinion mailed May 20, 2021", 5 pgs.

Avants, Brian B., et al., "Symmetric diffeomorphic image registration with cross-correlation: evaluating automated labeling of elderly and neurodegenerative brain", Medical image analysis 12.1, (2008), 1-29.

Balakrishnan, Guha, et al., "VoxelMorph: a learning framework for deformable medical image registration", IEEE transactions on medical imaging 38.8, (2019), 16 pgs.

Ganin, Yaroslav, et al., "Unsupervised domain adaptation by backpropagation", arXiv:1409.7495v2, (2015), 1-11.

He, Kaiming, et al., "Deep Residual Learning for Image Recognition", 2016 IEEE Conference on Computer Vision and Pattern Recognition, (2016), 770-778.

Huang, Gao, et al., "Densely connected convolutional networks", Proceedings of the IEEE conference on computer vision and pattern recognition, (2017), 4700-4708.

Kurenkov, Andrey, et al., "Deformnet: Free-form deformation network for 3d shape reconstruction from a single image", 2018 IEEE Winter Conference on Applications of Computer Vision (WACV). IEEE, (2018), 12 pgs.

Ronneberger, Olaf, et al., "U-Net Convolutional Networks for Biomedical Image Segmentation", Computer Science Department and BIOSS Centre for Biological Signalling Studies, University of Freiburg, Germany, (May 18, 2015), 234-241.

Sun, Baochen, et al., "Deep coral: Correlation alignment for deep domain adaptation", European conference on computer vision. Springer, Cham, (2016), 7 pgs.

Xu, Y, et al., "A method for volumetric imaging in radiotherapy using single x-ray projection", Med Phys vol. 42 No. 5, (May 2015), 2498-2509.

Zhang, Jun, "Inverse-consistent deep networks for unsupervised deformable image registration", arXiv preprint arXiv:1809.03443, (2018), 13 pgs.

\* cited by examiner ics (REAL-TIME MOTION MONITORING USING DEEP LEARNING)

PRIORITY

This application is a U.S. National Stage Filing under 35 U.S.C. § 371 from International Application No. PCT/CA2021/050316, filed on Mar. 10, 2021, and published as WO2021/184107 on Sep. 23, 2021, which claims the benefit of priority to U.S. Provisional Application No. 62/991,356, filed Mar. 18, 2020, titled "Real-Time Motion Monitoring Using Population-Based Deep Learning: the benefit of priority of each of which is hereby claimed herein, and which applications and publication are hereby incorporated herein by reference in their entireties.

TECHNICAL FIELD

Embodiments of the present disclosure pertain generally to medical image and artificial intelligence processing techniques. In particular, the present disclosure pertains to use of end-to-end deep learning for real-time motion monitoring.

BACKGROUND

In radiotherapy or radiosurgery, treatment planning is typically performed based on medical images of a patient and requires the delineation of target volumes and normal critical organs in the medical images. One challenge occurs with accurately tracking the various objects, such as a tumor, healthy tissue, or other aspects of patient anatomy when the patient is moving (e.g., breathing).

Current techniques are unable to directly measure in 3D a changing patient state in real-time. For example, some techniques use 2D imaging, such as 2D kV projections or 2D MRI slices, which are not able to completely track the various objects.

Other techniques may rely on detecting surface information, either directly or by tracking markers on a vest or a box affixed to the patient. These techniques assume that the surface information is correlated to internal patient state, which is often not accurate.

Yet other techniques may rely on implanting markers, such as magnetically tracked markers, or using x-ray detection of radio-opaque markers. These techniques are invasive and correspond only to limited points within the patient.

Regression models or other model-based techniques may be used to assist in motion monitoring. However, these techniques may be inaccurate or not able to track in real-time.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
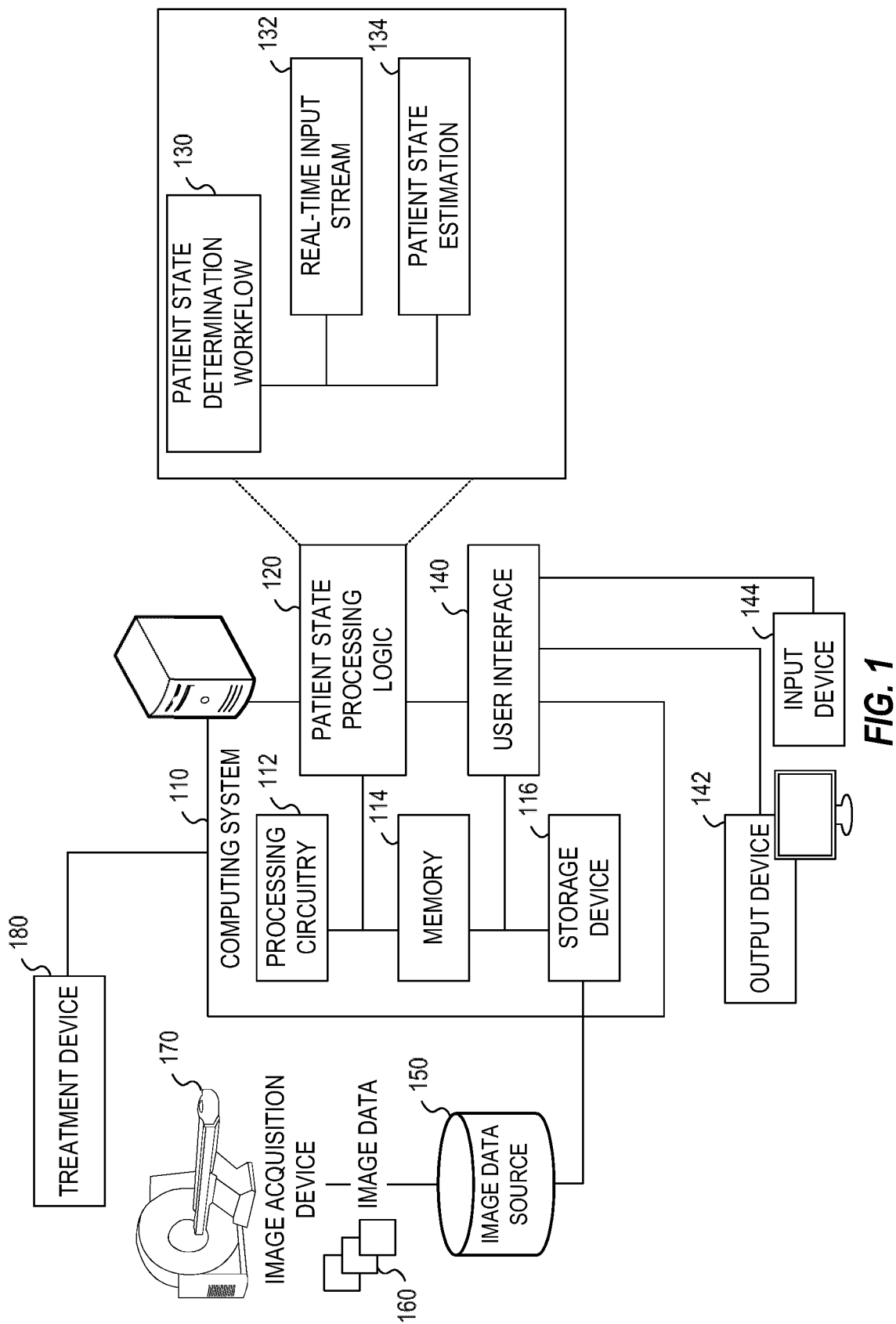
FIG. 1 illustrates an exemplary radiotherapy system adapted for performing image patient state estimation processing.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

In conventional radiotherapy, larger margins are needed to account for motion due to breathing, etc. With Image guided radiation therapy (IGRT) it is possible to obtain more accurate targeting, therefore margins can be reduced.

IGRT may use computed tomography (CT) imaging, cone beam CT (CBCT), magnetic resonance (MR) imaging, positron-emission tomography (PET) imaging, or the like to obtain a 3D or 4D image of a patient prior to irradiation. For example, a CBCT-enabled linac (linear accelerator) may consist of a kV source/detector affixed to the gantry at a 90 degree angle to a radiation beam, or a MR-Linac device may consist of a linac integrated directly with an MR scanner.

Localizing motion during the actual irradiation treatment delivery (intrafraction motion) may allow reduction of additional treatment margins that would otherwise be used to encompass motion, thus either allowing higher doses to be delivered, reduction of side-effects, or both. Many IGRT imaging technologies are generally not sufficiently fast for imaging intrafractional motion. For example, CBCT requires multiple kV images from various angles to reconstruct a full 3D patient image, and a 3D MR requires multiple 2D slices, or filling of the full 3D k-space, each which may take minutes to generate a full 3D volume.

In some cases, the real-time or quasi-real-time data that would usually be completely acquired prior to generation of a 3D IGRT image, may be used as it is gathered to estimate the instantaneous 3D volume at a much faster refresh rate from the incomplete, yet fast, stream of incoming information. For example, 2D kV projections, 2D MR slices, 2D CT slices, or other imaging modalities (or in some examples, non-image based information, such as breathing information) may be used to estimate a full 3D CBCT-like or 3D MR-like image that evolves with the actual patient motion during treatment. Although fast, on their own these 2D images provide only a limited perspective of the patient, not the full 3D picture.

A patient state generator may receive partial measurements (e.g., a 2D image) as an input and generate (e.g., estimate) a complete patient state (e.g., a 3D volume) as an output. Partial measurements may be received in a real-time as stream of images (e.g., 2D images) taken from a kV imager or a MR imager, for example. The kV imager may produce stereoscopic 2D images for the real-time stream (e.g., two x-ray images that are orthogonal and acquired substantially simultaneously). The kV imager may be fixed in a room or coupled to a treatment device (e.g., attached to a gantry). The MR imager may produce 2D MR slices, which may be orthogonal or parallel. A patient state may be generated from an image or a set of images (e.g., a pair of images, such as two orthogonal image planes, or two or more images, such as multiple parallel 2D image planes, such as using multi-slice 2D MR or CT images), received. For example, at any given moment in time, the patient state for the last received image from the real-time stream may be generated.

The patient model is a 4D dataset which contains a series of 3D patient states (3D volumes) varying according to one or several parameters, (e.g. breathing phase). This simplifies the modeling by allowing chunks of partial imaging data to be taken from different breathing cycles and assigned to a single representative breathing cycle. A 3D volume may then be reconstructed for each phase 'bin'.

In an example, the patient state may be represented, for example, as a 3D volume, or a 3D deformation vector field (DVF) plus a 3D reference image. These may be equivalent, since the elements of the 3D DVF and the 3D reference image may be used to obtain (e.g., deform the 3D reference image with the 3D DVF) the 3D volume. An output of the systems and methods described herein may include a 3D DVF to deform an input 3D reference image according to an input 2D image (e.g., from a real-time stream of images), to obtain a 3D volume of the current patient state.

FIG. 1 illustrates an exemplary radiotherapy system adapted for using deep neural networks for real-time motion monitoring. The real-time motion monitoring may be used to determine a patient state to enable the radiotherapy system to provide radiation therapy to a patient based on specific aspects of captured medical imaging data. The radiotherapy system includes an image processing computing system 110 which hosts patient state processing logic 120. The image processing computing system 110 may be connected to a network (not shown), and such network may be connected to the Internet. For instance, a network can connect the image processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170, and a treatment device 180 (e.g., a radiation therapy device). As an example, the image processing computing system 110 can be configured to perform image patient state operations by executing instructions or data from the patient state processing logic 120, as part of operations to generate and customize radiation therapy treatment plans to be used by the treatment device 180.

The image processing computing system 110 may include processing circuitry 112, memory 114, a storage device 116, and other hardware and software-operable features such as a user interface 140, communication interface, and the like.

The storage device 116 may store computer-executable instructions, such as an operating system, radiation therapy treatment plans (e.g., original treatment plans, adapted treatment plans, or the like), software programs (e.g., radiotherapy treatment plan software, artificial intelligence implementations such as deep learning models, machine learning models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the patient state processing logic 120 and the user interface 140). The instructions may also reside, completely or at least partially, within the memory 114 and/or within the processing circuitry 112 during execution thereof by the image processing computing system 110, with the memory 114 and the processing circuitry 112 also constituting machine-readable media.

The memory device 114 or the storage device 116 may constitute a non-transitory computer-readable medium. For example, the memory device 114 or the storage device 116 may store or load instructions for one or more software applications on the computer-readable medium. Software applications stored or loaded with the memory device 114 or the storage device 116 may include, for example, an operating system for common computer systems as well as for software-controlled devices. The image processing computing system 110 may also operate a variety of software programs comprising software code for implementing the patient state processing logic 120 and the user interface 140. Further, the memory device 114 and the storage device 116 may store or load an entire software application, part of a software application, or code or data that is associated with a software application, which is executable by the processing circuitry 112. In a further example, the memory device 114 or the storage device 116 may store, load, or manipulate one or more radiation therapy treatment plans, imaging data, patient state data, dictionary entries, artificial intelligence model data, labels and mapping data, etc. It is contemplated that software programs may be stored not only on the storage device 116 and the memory 114 but also on a removable computer medium, such as a hard drive, a computer disk, a CD-ROM, a DVD, a HD, a Blu-Ray DVD, USB flash drive, a SD card, a memory stick, or any other suitable medium; such software programs may also be communicated or received over a network.

Although not depicted, the image processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the image processing computing system 110 may obtain image data 160 from the image data source 150, for hosting on the storage device 116 and the memory 114. In an example, the software programs operating on the image processing computing system 110 may convert medical images of one format (e.g., MRI) to another format (e.g., CT), such as by producing synthetic images, such as a pseudo-CT image. In another example, the software programs may register or associate a patient medical image (e.g., a CT image or an MR image) with that patient's dose distribution of radiotherapy treatment (e.g., also represented as an image) so that corresponding image voxels and dose voxels are appropriately associated. In yet another example, the software programs may substitute functions of the patient images such as signed distance functions or processed versions of the images that emphasize some aspect of the image information. Such functions might emphasize edges or differences in voxel textures, or other structural aspects. In another example, the software programs may visualize, hide, emphasize, or de-emphasize some aspect of anatomical features, patient measurements, patient state information, or dose or treatment information, within medical images. The storage device 116 and memory 114 may store and host data to perform these purposes, including the image data 160, patient data, and other data required to create and implement a radiation therapy treatment plan and associated patient state estimation operations.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 160 to be received or obtained in memory 114, and processed using the patient state processing logic 120. For example, the image processing computing system 110 may receive image data 160 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing/simulation environment that uses a network to collaboratively perform the embodiments described herein. In addition, such network may be connected to internet to communicate with servers and clients that reside remotely on the internet.

In further examples, the processing circuitry 112 may utilize software programs (e.g., a treatment planning software) along with the image data 160 and other patient data to create a radiation therapy treatment plan. In an example, the image data 160 may include 2D or 3D volumes, such as from a CT or MR. In addition, the processing circuitry 112 may utilize deep neural networks to generate an estimated patient state.

Further, such software programs may utilize patient state processing logic 120 to implement a patient state determination workflow 130, using the techniques further discussed herein. The processing circuitry 112 may subsequently then transmit the executable radiation therapy treatment plan via a communication interface and the network to the treatment device 180, where the radiation therapy plan will be used to treat a patient with radiation via the treatment device, consistent with results of the patient state determination workflow 130. Other outputs and uses of the software programs and the patient state determination workflow 130 may occur with use of the image processing computing system 110.

As discussed herein (e.g., with reference to the patient state determination discussed herein), the processing circuitry 112 may execute a software program that invokes the patient state processing logic 120 to implement functions including deep neural networks.

In an example, the image data 160 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 160 may also include or be associated with auxiliary information, such as segmentations/contoured images, or dose images. In an example, the image data 160 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 160 may be received and stored in any type of data or any type of format (e.g., in a Digital Imaging and Communications in Medicine (DICOM) format) that the image acquisition device 170 and the image processing computing system 110 may use to perform operations consistent with the disclosed embodiments.

In an example, the image acquisition device 170 may be integrated with the treatment device 180 as a single apparatus (e.g., an MRI device combined with a linear accelerator, also referred to as an "MR-linac", as shown and described in FIG. 3 below). Such an MR-linac can be used, for example, to precisely determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The image processing computing system 110 may communicate with an external database through a network to send/receive a plurality of various types of data related to image processing and radiotherapy operations. For example, an external database may include machine data that is information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The image processing computing system 110 can collect and obtain data, and communicate with other systems, via a network using one or more communication interfaces, which are communicatively coupled to the processing circuitry 112 and the memory 114. For instance, a communication interface may provide communication connections between the image processing computing system 110 and radiotherapy system components (e.g., permitting the exchange of data with external devices). For instance, the communication interface may in some examples have appropriate interfacing circuitry from an output device 142 or an input device 144 to connect to the user interface 140, which may be a hardware keyboard, a keypad, or a touch screen through which a user may input information into the radiotherapy system.

As an example, the output device 142 may include a display device which outputs a representation of the user interface 140 and one or more aspects, visualizations, or representations of the medical images. The output device 142 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D volume), or any related information to the user. The input device 144 connected to the user interface 140 may be a keyboard, a keypad, a touch screen or any type of device that a user may input information to the radiotherapy system. Alternatively, the output device 142, the input device 144, and features of the user interface 140 may be integrated into a single device such as a smartphone or tablet computer, e.g., Apple iPad®, Lenovo Thinkpad®, Samsung Galaxy®, etc.

Furthermore, any and all components of the radiotherapy system may be implemented as a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the image processing computing system 110, the image data sources 150, or like components, may be implemented as a virtual machine or within a cloud-based virtualization environment.

The patient state processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 160 obtained from one or more patients via the image acquisition device 170. The image data source 150 or other databases may also store data to be used by the patient state processing logic 120 when executing a software program that performs patient state estimation operations, or when creating radiation therapy treatment plans. Further, various databases may store machine learning models, including the network parameters constituting the model learned by the network and the resulting predicted data. The image processing computing system 110 thus may obtain and/or receive the image data 160 (e.g., 2D MRI slice images, CT images, 2D Fluoroscopy images, X-ray images, 3D MRI images, 4D MRI images, etc.) from the image data source 150, the image acquisition device 170, the treatment device 180 (e.g., a MRI-Linac), or other information systems, in connection with performing image patient state estimation as part of treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "real-time" while a patient is undergoing radiation therapy treatment, for example, when using the treatment device 180 (with "real-time" meaning acquiring the data in 10 milliseconds or less). In another example for some applications, real-time may include a timeframe within (e.g., up to) 200 or 300 milliseconds. In an example, real-time may include a time period fast enough for a clinical problem being solved by techniques described herein. In this example, real-time may vary depending on target speed, radiotherapy margins, lag, response time of a treatment device, etc.

The patient state processing logic 120 in the image processing computing system 110 is depicted as implementing a patient state determination workflow 130 with various deep neural networks and estimation of a patient state (e.g., a DVF). In an example, the patient state determination workflow 130 operated by the patient state processing logic 120 uses a real-time input stream 132 (e.g., 2D partial measurements, such as from a CT or MR) to estimate a patient state with the patient state 134 being represented in an example by a DVF.

Figure 2:
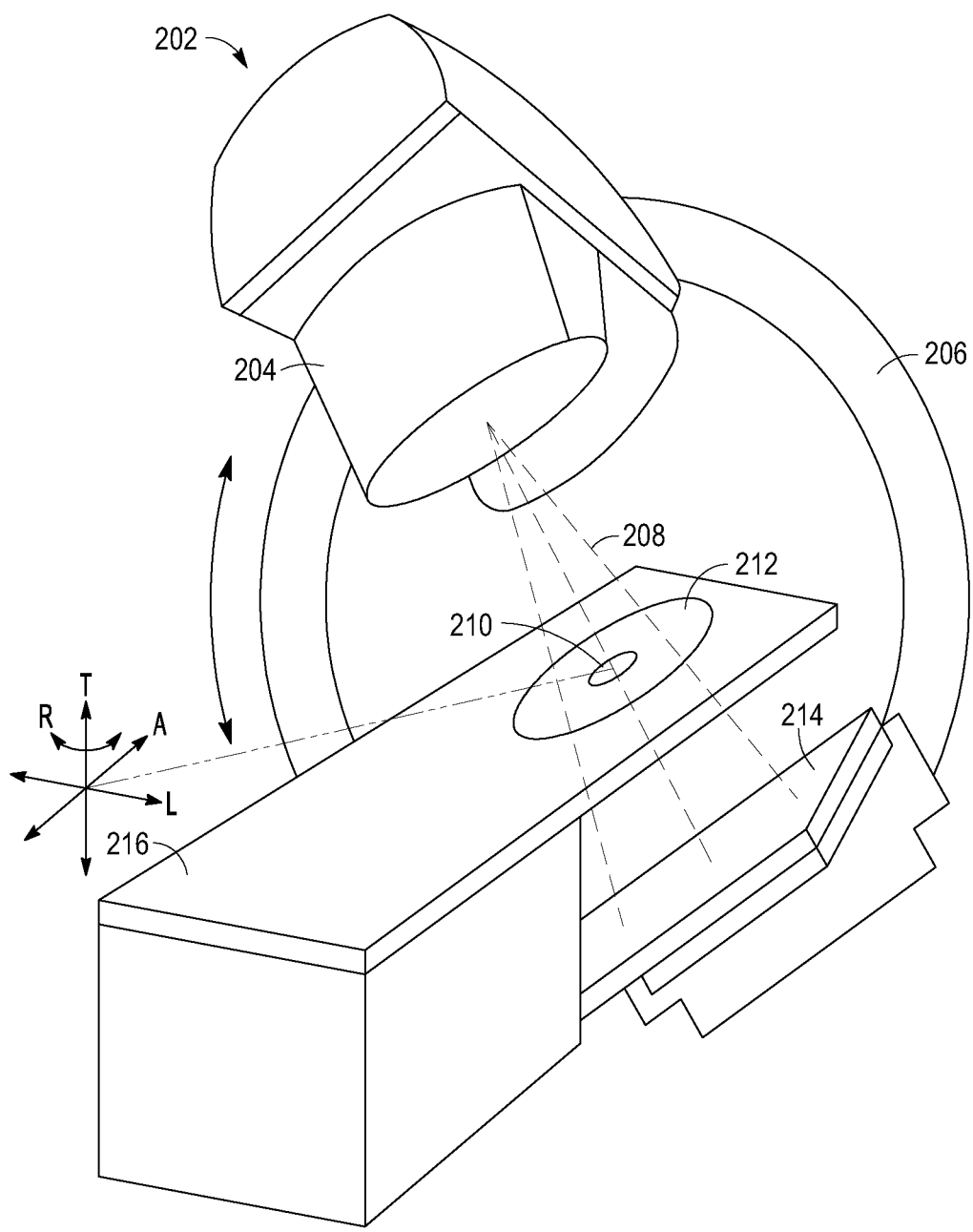
FIG. 2 illustrates an exemplary image-guided radiotherapy device.

FIG. 2 illustrates an exemplary image-guided radiotherapy device 202, that includes include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

As an example, a patient may be positioned in a region 212, supported by the treatment couch 216 to receive a radiation therapy dose according to a radiation therapy treatment plan (e.g., a treatment plan generated by the radiotherapy system of FIG. 1). The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an example, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within the radiotherapy system or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, an MR-linac, or radiotherapy portal imaging device, etc., as would be recognized by one of ordinary skill in the art.

Figure 3:
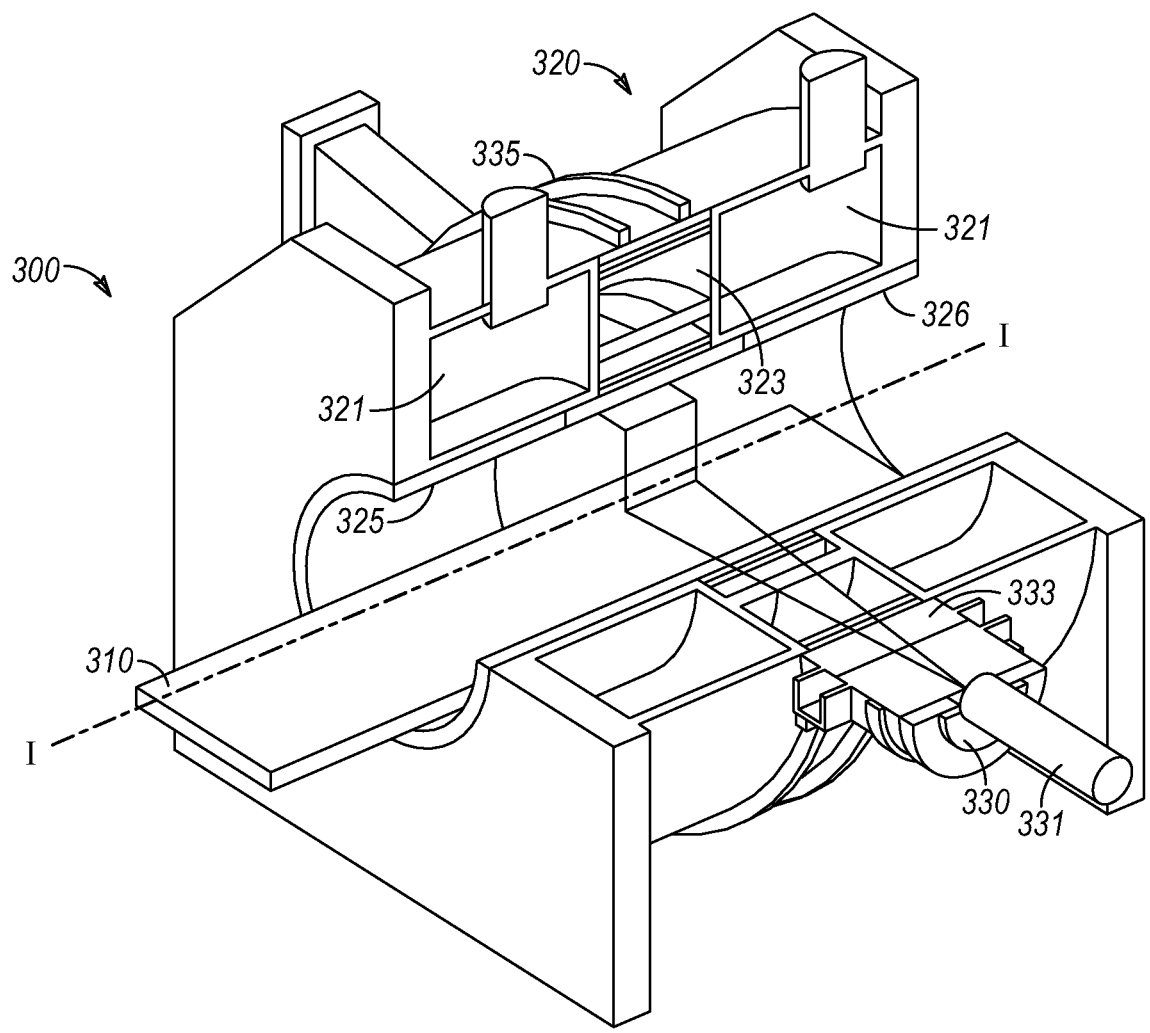
FIG. 3 illustrates a partially cut-away view of an exemplary system including a combined radiation therapy system and an imaging system, such as a nuclear magnetic resonance (MR) imaging system.

FIG. 3 depicts an exemplary radiation therapy system 300 (e.g., known in the art as a MR-Linac) that can include combining a radiation therapy device 202 and an imaging system, such as a nuclear magnetic resonance (MR) imaging system consistent with the disclosed embodiments. As shown, system 300 may include a couch 310, an image acquisition device 320, and a radiation delivery device 330. System 300 delivers radiation therapy to a patient in accordance with a radiotherapy treatment plan. In some embodiments, image acquisition device 320 may correspond to image acquisition device 170 in FIG. 1 that may acquire images.

Couch 310 may support a patient (not shown) during a treatment session. In some implementations, couch 310 may move along a horizontal, translation axis (labelled "I"), such that couch 310 may move the patient resting on couch 310 into or out of system 300. Couch 310 may also rotate around a central vertical axis of rotation, transverse to the translation axis. To allow such movement or rotation, couch 310 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321, and may be displaced along that central axis. The displacement may create a gap, or window, between coils 325 and 326. In the embodiments where magnet 321 also includes a central window 323 between coils, the two windows may be aligned with each other.

Image acquisition is used to track tumor movement. At times, internal or external surrogates may be used. However, implanted seeds may move from their initial positions or become dislodged during radiation therapy treatment. Also, using surrogates assumes there is a correlation between tumor motion and the displacement of the external surrogate. However, there may be phase shifts between external surrogates and tumor motion, and their positions frequently lose correlation over time. It is known that there may be mismatches between tumor and surrogates upward of 9 mm. Further, any deformation of the shape of a tumor is unknown during tracking.

An advantage of magnetic resonance imaging (MRI) is in the superior soft tissue contrast that is provided to visualize the tumor in more detail. Using a plurality of intra-fractional MR images allows the determination of both shape and position (e.g., centroid) of a tumor. In addition, MRI images improve any manual contouring performed by, for example, a radiation oncologist, even when auto-contouring software (e.g., ABAS®) is utilized. This is because of the high contrast between the tumor target and the background region provided by MR images.

Another advantage of using an MR-Linac system is that a treatment beam can be continuously on and thereby executing intra-fractional tracking of the target tumor. For instance, optical tracking devices or stereoscopic x-ray fluoroscopy systems can detect tumor position at 30 Hz by using tumor surrogates. With MRI, the imaging acquisition rates are faster (e.g., 3-6 fps). Therefore, the centroid position of the target may be determined, artificial intelligence (e.g., neural network) software can predict a future target position. An added advantage of intra-fractional tracking by using an MR-Linac is that the by being able to predict a future target location, the leaves of the multi-leaf collimator (MLC) will be able to conform to the target contour a its predicted future position. Thus, predicting future tumor position using MRI occurs at the same rate as imaging frequency during tracking. By being able to track the movement of a target tumor clearly using detailed MRI imaging allows for the delivery of a highly conformal radiation dose to the moving target.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 320 concerns certain embodiments and is not intended to be limiting.

Radiotherapy device 330 may include the source of radiation 331, such as an X-ray source or a linear accelerator, and a multi-leaf collimator (MLC) 333. Radiotherapy device 330 may be mounted on a chassis 335. One or more chassis motors (not shown) may rotate chassis 335 around couch 310 when couch 310 is inserted into the treatment area. In an embodiment, chassis 335 may be continuously rotatable around couch 310, when couch 310 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 310, image acquisition device 320, and radiotherapy device 330. The control circuitry of radiotherapy device 330 may be integrated within system 300 or remote from it.

During a radiotherapy treatment session, a patient may be positioned on couch 310. System 300 may then move couch 310 into the treatment area defined by magnetic coils 321, 325, 326, and chassis 335. Control circuitry may then control radiation source 331, MLC 333, and the chassis motor(s) to deliver radiation to the patient through the window between coils 325 and 326 according to a radiotherapy treatment plan.

Figure 4:
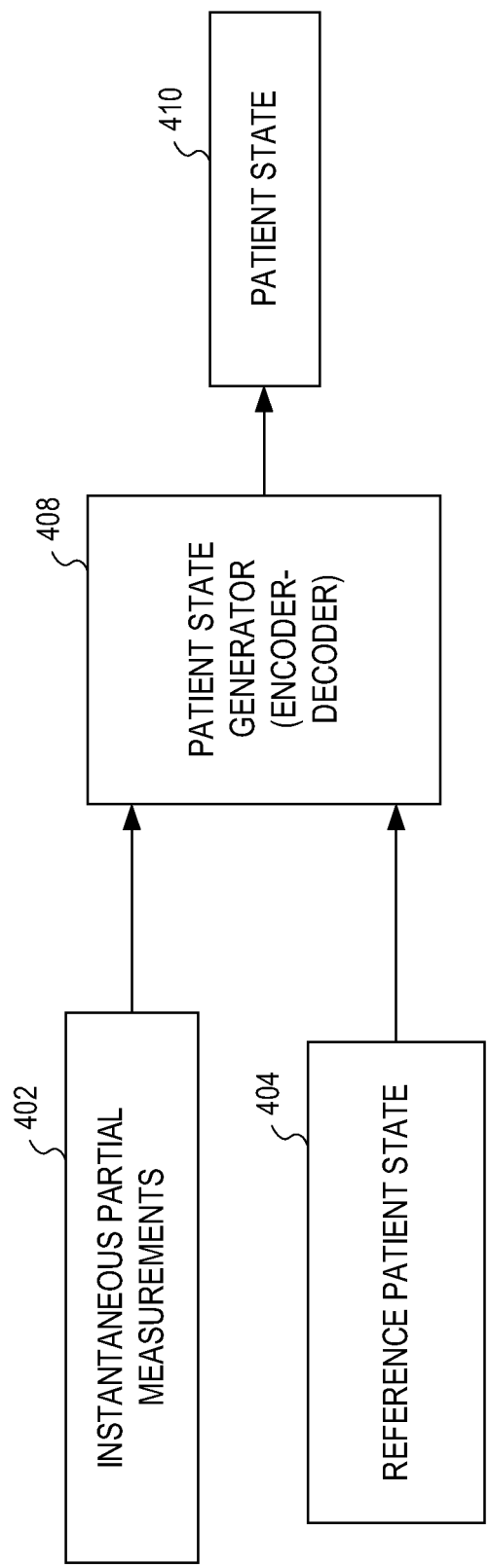
FIG. 4 illustrates an exemplary flow diagram for estimating a patient state using partial measurements and a reference patient state.

FIG. 4 illustrates an exemplary flow diagram for estimating a patient state. FIG. 4 includes a patient state generator 408 for estimating a patient state using an encoder-decoder convolutional neural network (CNN) or other neural network. The patient state generator 408 uses an instantaneous partial measurement 402 and a reference patient state of a patient 404 to estimate a patient state, output at block 410. The reference patient state 404 is generated using previous measurements, including previous patient states corresponding to the previous measurements. The input to the patient state generator 408 may include a 3D volume (e.g., from the reference patient state 404) and a 2D image (e.g., from the instantaneous partial measurement 402). During a training step, 4D datasets (e.g., series of 3D volumes (or patient states)) are used to train a model so that the model learns appropriate type of bodily motion. In an example, after the model is trained, the 4D datasets are no longer needed or used. During treatment, a single 3D reference volume is used input to the network (along with a 2D image) to generate patient state estimates.

In practical radiotherapy applications, partial measurements (e.g., a 2D image or image slice) provide incomplete information about the patient state (e.g., a 3D volume). For example, a 2D MRI slice is a single cut through a 3D representation of the patient, and an x-ray projection is an integration through voxels along ray-lines of a 3D representation. Using either image results in impartial information (e.g., a 2D image rather than a 3D representation of patient anatomy). The patient state generator 408 may use the partial information and the reference patient state 404 generated from past measurements and/or offline (pre-treatment) acquisitions to estimate the patient state 410. The patient state generator 408 may include creation of a low dimensional patient state representation.

4D images may include a series of 3D volumes of a representative respiratory cycle. For example, for a 4D CBCT, a number of X-ray projections are acquired and sorted into a number of bins. Sorting may be done, for example, by detecting a diaphragm position in each projection directly in the images, or using a separate respiratory signal acquired simultaneously with the kV projections, and binning the projection according to the phase or amplitude of the signal. Each bin is then reconstructed separately with the kV projections assigned to that bin to form a 3D volume per bin. Similar techniques may be used to generate a 4D MR image. A model may then be constructed using the 4D image as an interim step. In some cases the interim step of reconstructing a 4D image may not be necessary, and the low dimensional state representation may be created directly from the measurements.

Patient state generators (e.g. 408) producing an output DVF provide a mechanism for deforming a reference patient state (e.g., as well as additional information as defined on a 3D reference image) to the estimated current patient state. A DVF-based motion model may be a parameterization (e.g. a principal component analysis (PCA)) of the DVFs extracted from one or several 4D datasets.

The systems and methods described herein include a deep learning framework for mapping instantaneous partial measurements (e.g., 2D images) to their underlying complete 3D patient states (e.g., output estimates).

The systems and methods described herein include an end-to-end deep-learning framework using convolutional neural networks (CNNs) for patient state generation. Specifically, given an instantaneous partial measurement of the patient state (in our preferred embodiment, a 2D image) and a 3D reference volume, a fully 3D deformation vector field (DVF) is estimated which characterizes the full per-voxel motion of the 3D reference volume to the current 3D patient state. Conventional machine learning methods may also be used for 2D to 3D inference between instantaneous partial measurements (2D) and the corresponding 3D patient states. However, these latter methods usually suffer from two primary limitations:

Limitation 1: For each individual patient, a patient model (4D dataset) must be acquired, and a subject-specific patient state generator for 2D to 3D inference must be trained. Lengthy image acquisition as well as long image processing (e.g. 3D deformable image registration) and model training times can negatively impact treatment workflow.

Limitation 2: A restrictive patient motion model (e.g. using principal component analysis) is usually required to facilitate inference between 2D and 3D patient states, which limits the capacity of the patient state generator to accommodate complex/local motion (e.g. liver drift over treatment duration).

To address these limitations, the systems and methods described herein include an end-to-end deep-learning framework to directly perform 2D to 3D inference. To address the first limitation, during training, the network is trained on a population of 4D patient models. However, once trained, the network can be used to generate fully 3D patient state estimations given only an instantaneously acquired 2D image and an arbitrary 3D reference volume. Furthermore, our patient state generator is only trained once, but can adapt to other patients, as the generator is conditioned on a 3D reference volume. Optionally, if a 4D patient model is available, the pre-trained patient state generator network can be quickly fine-tuned, prior to treatment, in order to optimize performance on the given patient.

To address the second limitation, the systems and methods described herein do not explicitly parameterize motion between phases of the patient model, but rather directly estimate full 3D DVFs consistent with observed 2D images. This allows considerably more freedom in the type of motion that can be expressed within the proposed patient state generator, particularly in comparison with recent model-based methods relying on linear motion models (e.g. principal component analysis).

Figure 5:
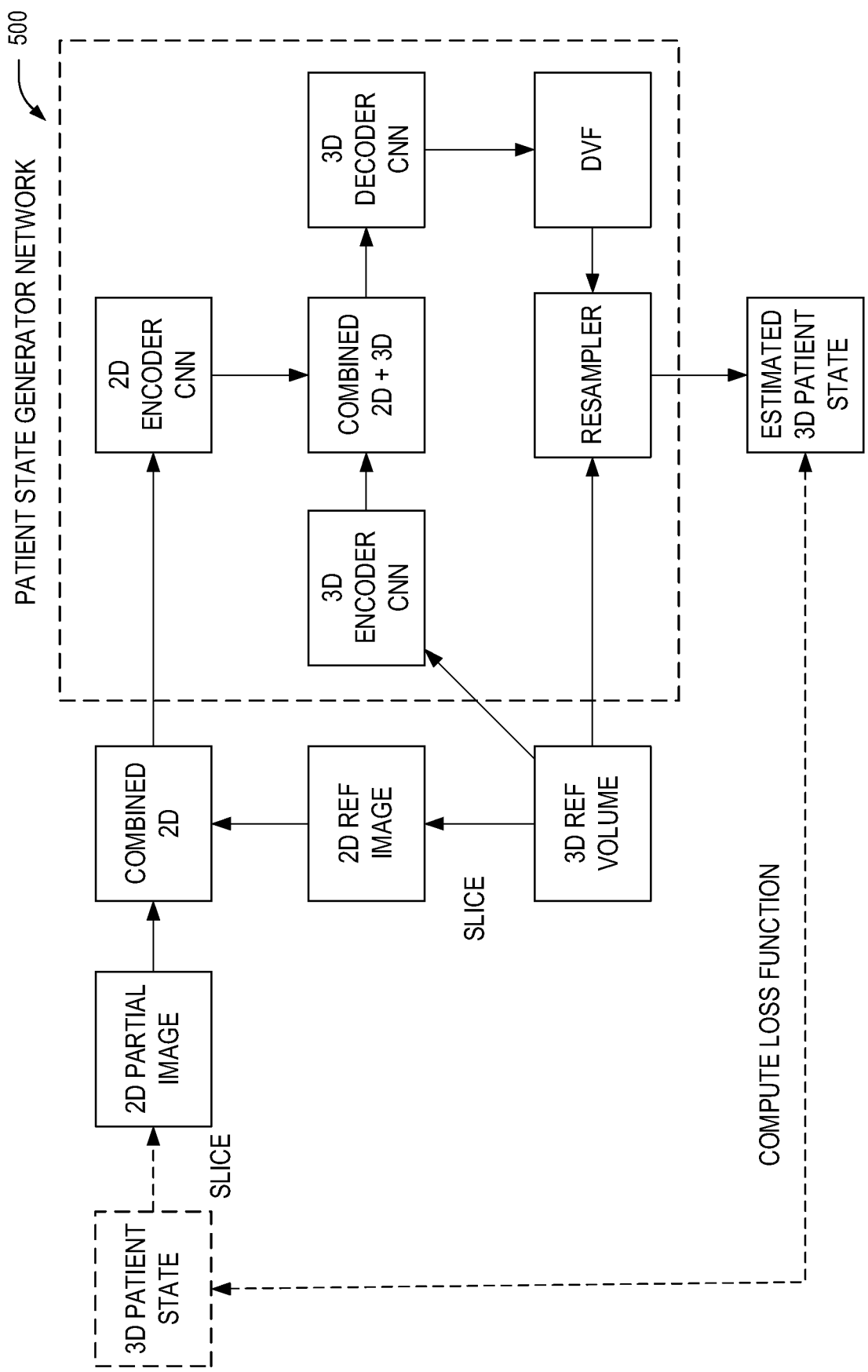
FIG. 5 illustrates an exemplary block diagram showing a patient state generator using based on convolutional neural networks.

A high-level overview of a convolutional neural network for patient state generation is presented in FIG. 5. The network architecture consists of three primary modules: the 2D encoder, the 3D encoder, and the 3D decoder. The network as whole accepts as input a multi-channel 2D partial measurement image and a 3D reference volume. In the preferred embodiment, the 2D partial measurement image is a single plane acquisition using magnetic resonance imaging, or multiple planes (either orthogonal or parallel) may be used. In other embodiments, it may be a projection image (e.g. using CBCT).

FIG. 5 illustrates an exemplary block diagram 500 showing a patient state generator using based on convolutional neural networks.

The end-to-end patient state generator of block diagram 500 may be based on convolutional neural networks. The network accepts as input a multi-channel 2D partial measurement image, a 3D reference volume, and returns a DVF characterizing the relative 3D motion between the reference volume and optionally the 3D patient state, as well as an estimate of the 3D patient state. The solid lines represent the action of the patient state generator during inference only, while the dashed lines represent additional steps carried out during the training phase. The 3D patient state may be omitted when applied online or in real-time (and the loss function may not be known as well).

The 2D encoder is responsible for processing the multi-channel 2D image into a low-dimensional latent (hidden) space. It consists of repeated applications of convolutional layers (advanced convolutional blocks could also be used in place of standard convolutional layers) and down-sampling operations. The multi-channel 2D image input consists of the concatenation of two 2D images: the instantaneous partial 2D image, as well as the 3D reference volume sliced and resampled to the same specifications as the former. Therefore, the 2D input contains information about the motion (relative to the reference state) occurring in the 2D plane of acquisition. The 3D encoder is similarly responsible for processing the 3D reference volume input into a low-dimensional latent space. These latent representations are then combined (e.g. by projection to a common space followed by summation or concatenation). In an example, any number of convolutional blocks or down-sampling/up-sampling operations may be used in the encoder/decoder branches.

The combined latent representation is then decoded by the 3D decoder into a full 3D DVF. Skip connections (e.g., as described below in FIG. 6) between the 3D encoder and 3D decoder may also be optionally used in this stage. Finally, the 3D DVF is used to resample the 3D reference volume, producing the estimated 3D patient state.

A training procedure may include operations described below.

The 2D encoder, 3D encoder, 3D decoder, and resampling modules are contained in a single network (the patient state generator network) which can be trained end-to-end in an iterative fashion using any appropriate deep-learning library (e.g. PyTorch or Tensorflow). A multi-patient training set of 4D patient models is required for training. The network is trained using training triplets each consisting of a 3D reference volume, a 3D target volume (or patient state), and an instantaneous (2D) partial measurement of the corresponding patient state.

To generate a training triplet, both the 3D reference and target volumes are randomly sampled from a randomly chosen 4D patient model (e.g. each volume characterizing one phase of a respiratory cycle) from the multi-patient training set. A slice (single plane 2D image) is extracted from the chosen 3D reference and target volumes resampled to the specifications of the instantaneously acquired 2D images acquired during treatment (FIG. 1). These two images are then concatenated to form a multi-channel 2D image. Together with the chosen 3D reference volume, they are fed into the network, the latter producing a DVF and a corresponding estimate of the chosen 3D target volume. This procedure is repeated (either prior to training, or on-the-fly during training) to generate a wide variety of training examples with which to train the network.

Several loss functions must be defined in order to optimize the network parameters. First, a loss function which maximizes the similarity between the actual 3D target volume and the estimated 3D target volume must be chosen (dashed line at bottom of FIG. 5). Example similarity functions include the sum of squared differences or the (local or global) normalized cross-correlation. Second, auxiliary loss functions which promote the generation of smooth DVFs may also be used. Example such loss functions include the L1 or L2 norm on DVF spatial gradients, and/or inverse consistency constraints.

Figure 6:
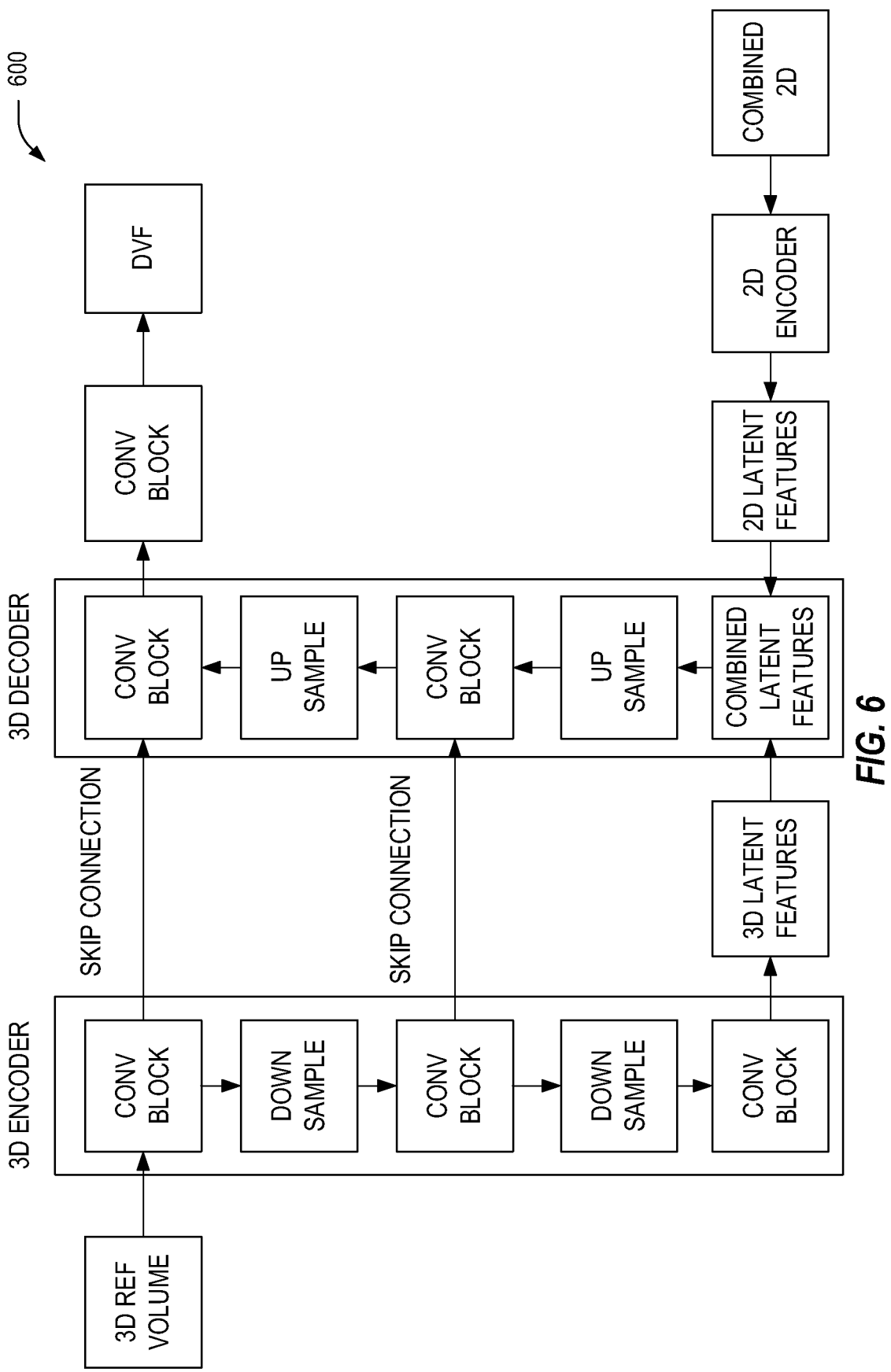
FIG. 6 illustrates an exemplary block diagram showing skip connections.

FIG. 6 illustrates an exemplary block diagram 600 showing skip connections.

The block diagram 600 includes an example use of skip connections between the 3D encoder and 3D decoder in the proposed patient model generator network. Each down/up-sampling operator reduces/increases the spatial resolution of the input feature maps, respectively. Using skip connections, feature maps from the encoding path are joined (using e.g. summation or concatenation) to the corresponding resolution feature maps from the decoding path to retain high-frequency spatial information and to improve the convergence properties of the neural network during training. We note that, in practice, any number of convolutional blocks or down/up-sampling operators may be used in the decoder/encoder, respectively.

Figure 7:
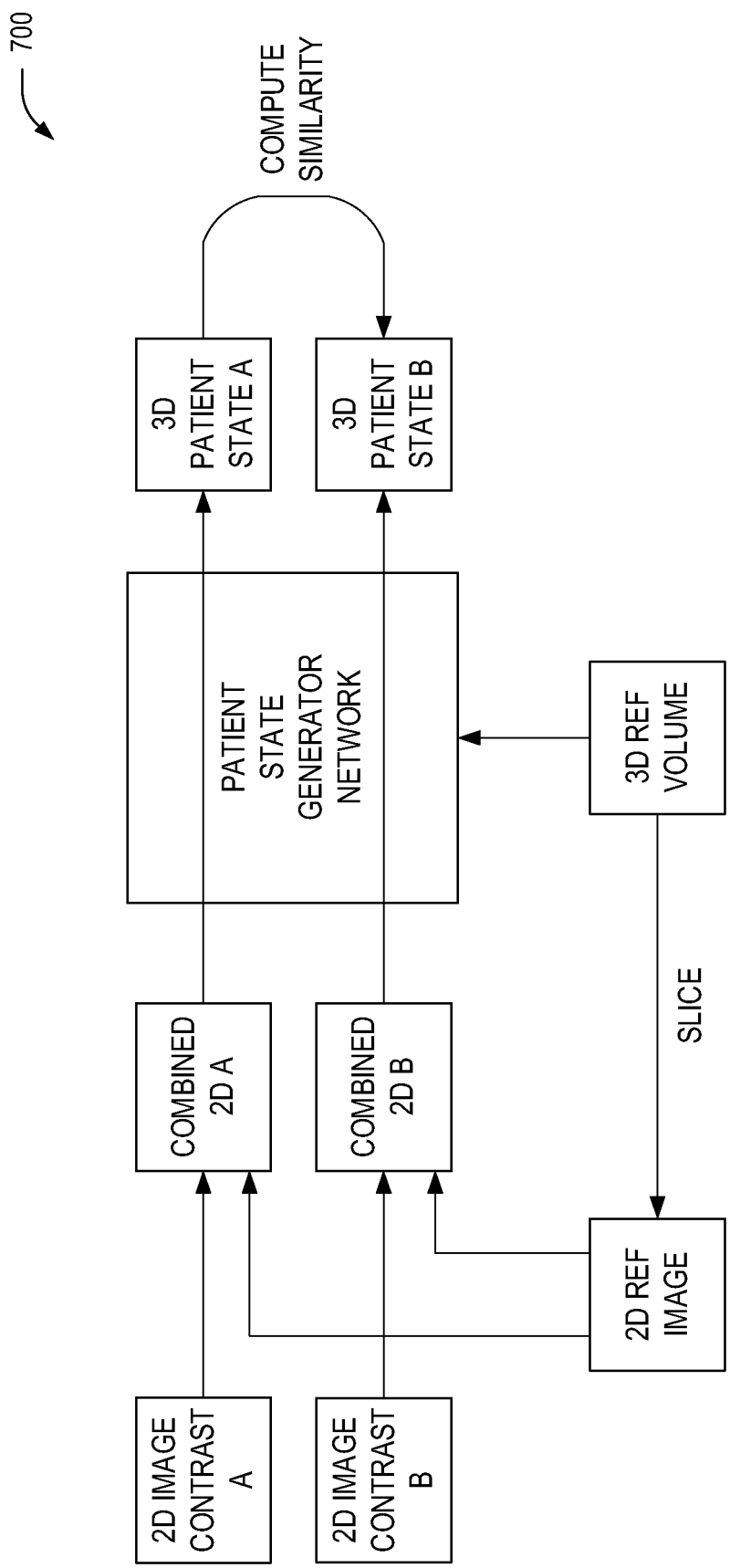
FIG. 7 illustrates an exemplary block diagram for domain adaptation for a patient state generator network.

FIG. 7 illustrates an exemplary block diagram for domain adaptation for a patient state generator network.

An example embodiment of the use of domain adaptation to increase robustness of trained patient state generator network to differences in 2D image contrast. Here, two 2D images of the same patient state, but characterized by different contrasts (A and B) are used as input into the network, producing two patient state estimations. Minimizing the differences between the two patient state estimations encourages the network to ignore the relevant contrast differences between the paired 2D images.

Once trained, the patient state generator network can be used to produce, in real-time, patient state estimates given a 3D reference volume and instantaneously acquired 2D images during treatment. In practice, the image contrast of the 2D input images may differ between the training phase and the real-time tracking phase (e.g. due to different pulse acquisition parameters, in the case of MR imaging), leading to degraded motion estimation. To alleviate this problem, unsupervised domain adaptation methods can be used to increase the robustness of the trained network to the relevant contrast differences. For example, given a patient for which two series of 2D images with different contrasts are available, pairs of cross-contrast 2D images, for which the displayed anatomy is similar, can be found. These matched image pairs can then be used to drive an additional consistency penalty loss during training. Other unsupervised domain adaptation methods (e.g. adversarial methods) may also be used. In another example, image-to-image translation models may be used to map images of one contrast to another.

Figure 8:
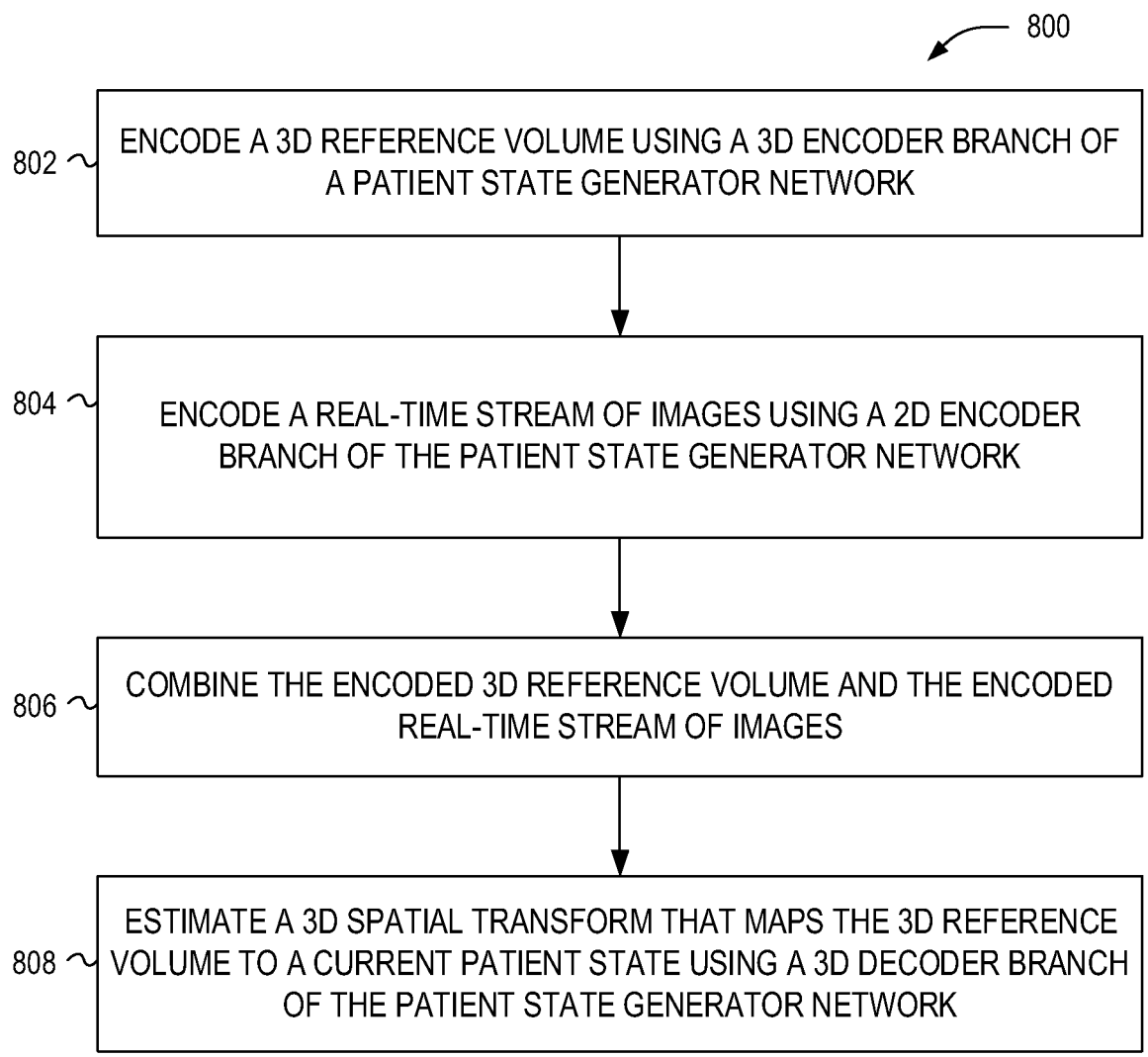
FIG. 8 a flowchart of exemplary operations for estimating a patient state during a radiation therapy procedure.

FIG. 8 illustrates a flowchart 800 of exemplary operations for estimating a patient state, for example during a radiation therapy treatment. The flowchart 800 may include operations to receive a 3D reference volume. The flowchart 800 may include an operation to receive a stream of images, for example from an image acquisition device. The stream of images may be received in real-time or during the radiation therapy treatment. In an example, the following operations are performed using a hardware processor to implement a patient state generator network. For example, the patient state generator network may be trained as a single neural network.

The flowchart 800 includes an operation 802 to encode the 3D reference volume using a 3D encoder branch of the patient state generator network. In an example, the 3D reference volume is a 3D magnetic resonance (MR) image or a 3D computed tomography (CT) image. In an example, the 3D reference volume is captured prior to the real-time stream of images or before the radiation therapy treatment.

The flowchart 800 includes an operation 804 to encode the real-time stream of images using a 2D encoder branch of the patient state generator network. The real-time stream of images may include a stream of slices of magnetic resonance (MR) images or kV projection (X-ray) images.

The flowchart 800 includes an operation 806 to combine the encoded 3D reference volume and the encoded real-time stream of images.

The flowchart 800 includes an operation 808 to estimate a 3D spatial transform that maps the 3D reference volume to a current patient state using a 3D decoder branch of the patient state generator network. In an example, the 3D spatial transform is a deformation vector field (DVF). The 3D reference volume and the real-time stream of images may be used as input to the single neural network, and the 3D spatial transform may be an output of the single neural network The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Example 1 is a method for estimating a patient state comprising: receiving a 3D reference volume; receiving a real-time stream of images from an image acquisition device; using a hardware processor to implement a patient state generator network to: encode the 3D reference volume using a 3D encoder branch of the patient state generator network; encode the real-time stream of images using a 2D encoder branch of the patient state generator network; combine the encoded 3D reference volume and the encoded real-time stream of images; and estimate a 3D spatial transform that maps the 3D reference volume to a current patient state using a 3D decoder branch of the patient state generator network.

In Example 2, the subject matter of Example 1 includes, wherein the 3D spatial transform is a deformation vector field (DVF).

In Example 3, the subject matter of Examples 1-2 includes, wherein the real-time stream of images is a stream of slices of magnetic resonance (MR) images or a kV projection image (X-ray).

In Example 4, the subject matter of Examples 1-3 includes, wherein the 3D reference volume is a 3D magnetic resonance (MR) image or a 3D computed tomography (CT) image.

In Example 5, the subject matter of Examples 1-4 includes, wherein the patient state generator network is trained as a single neural network.

In Example 6, the subject matter of Example 5 includes, wherein the 3D reference volume and the real-time stream of images are used as input to the single neural network, and wherein the 3D spatial transform is an output of the single neural network.

In Example 7, the subject matter of Examples 1-6 includes, wherein the 3D reference volume is captured prior to the real-time stream of images.

In Example 8, the subject matter of Examples 1-7 includes, wherein the real-time stream of images is received during a radiation therapy treatment.

Example 9 is a method for estimating a patient state comprising: using a hardware processor to implement a patient state generator network to: encode a 3D reference volume using a 3D encoder branch of the patient state generator network; encode a stream of images received during a radiation therapy treatment using a 2D encoder branch of the patient state generator network; combine the encoded 3D reference volume and the encoded real-time stream of images; and estimate a 3D spatial transform that maps the 3D reference volume to a current patient state using a 3D decoder branch of the patient state generator network.

In Example 10, the subject matter of Example 9 includes, wherein the 3D spatial transform is a deformation vector field (DVF).

In Example 11, the subject matter of Examples 9-10 includes, wherein the stream of images is a stream of slices of magnetic resonance (MR) images or a kV projection image (X-ray).

In Example 12, the subject matter of Examples 9-11 includes, wherein the 3D reference volume is a 3D magnetic resonance (MR) image or a 3D computed tomography (CT) image.

In Example 13, the subject matter of Examples 9-12 includes, wherein the patient state generator network is trained as a single neural network.

In Example 14, the subject matter of Example 13 includes, wherein the 3D reference volume and the stream of images are used as input to the single neural network, and wherein the 3D spatial transform is an output of the single neural network.

In Example 15, the subject matter of Examples 9-14 includes, wherein the 3D reference volume is captured prior to the radiation therapy treatment.

Example 16 is a system for estimating a patient state comprising: a hardware processor; memory including instructions, which when executed by the hardware processor, cause the hardware processor to implement a patient state generator network to: encode a 3D reference volume using a 3D encoder branch of the patient state generator network; encode the real-time stream of images using a 2D encoder branch of the patient state generator network; combine the encoded 3D reference volume and the encoded real-time stream of images; and estimate a 3D spatial transform that maps the 3D reference volume to a current patient state using a 3D decoder branch of the patient state generator network.

In Example 17, the subject matter of Example 16 includes, wherein the 3D spatial transform is a deformation vector field (DVF).

In Example 18, the subject matter of Examples 16-17 includes, wherein the real-time stream of images is a stream of slices of magnetic resonance (MR) images or a kV projection image (X-ray).

In Example 19, the subject matter of Examples 16-18 includes, wherein the 3D reference volume is a 3D magnetic resonance (MR) image or a 3D computed tomography (CT) image.

In Example 20, the subject matter of Examples 16-19 includes, wherein the patient state generator network is trained as a single neural network.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:
1. A method for estimating a patient state comprising:
receiving a 3D reference volume;
receiving a real-time stream of images from an image acquisition device;
using a hardware processor to implement a patient state generator network to:
encode the 3D reference volume using a 3D encoder branch of the patient state generator network;
encode the real-time stream of images using a 2D encoder branch of the patient state generator network;
combine the encoded 3D reference volume and the encoded real-time stream of images; and estimate a 3D spatial transform that maps the 3D reference volume to a current patient state using a 3D decoder branch of the patient state generator network.

2. The method of claim 1, wherein the 3D spatial transform is a deformation vector field (DVF).

3. The method of claim 1, wherein the real-time stream of images is a stream of slices of magnetic resonance (MR) images or a kV projection image (X-ray).

4. The method of claim 1, wherein the 3D reference volume is a 3D magnetic resonance (MR) image or a 3D computed tomography (CT) image.

5. The method of claim 1, wherein the patient state generator network is trained as a single neural network.

6. The method of claim 5, wherein the 3D reference volume and the real-time stream of images are used as input to the single neural network, and wherein the 3D spatial transform is an output of the single neural network.

7. The method of claim 1, wherein the 3D reference volume is captured prior to the real-time stream of images.

8. The method of claim 1, wherein the real-time stream of images is received during a radiation therapy treatment.

9. A method for estimating a patient state comprising:
using a hardware processor to implement a patient state generator network to:
encode a 3D reference volume using a 3D encoder branch of the patient state generator network;
encode a stream of images received during a radiation therapy treatment using a 2D encoder branch of the patient state generator network;
combine the encoded 3D reference volume and the encoded real-time stream of images; and
estimate a 3D spatial transform that maps the 3D reference volume to a current patient state using a 3D decoder branch of the patient state generator network.

10. The method of claim 9, wherein the 3D spatial transform is a deformation vector field (DVF).

11. The method of claim 9, wherein the stream of images is a stream of slices of magnetic resonance (MR) images or a kV projection image (X-ray).

12. The method of claim 9, wherein the 3D reference volume is a 3D magnetic resonance (MR) image or a 3D computed tomography (CT) image.

13. The method of claim 9, wherein the patient state generator network is trained as a single neural network.

14. The method of claim 13, wherein the 3D reference volume and the stream of images are used as input to the single neural network, and wherein the 3D spatial transform is an output of the single neural network.

15. The method of claim 9, wherein the 3D reference volume is captured prior to the radiation therapy treatment.

16. A system for estimating a patient state comprising:
a hardware processor;
memory including instructions, which when executed by the hardware processor, cause the hardware processor to implement a patient state generator network to:
encode a 3D reference volume using a 3D encoder branch of the patient state generator network;
encode the real-time stream of images using a 2D encoder branch of the patient state generator network;
combine the encoded 3D reference volume and the encoded real-time stream of images; and
estimate a 3D spatial transform that maps the 3D reference volume to a current patient state using a 3D decoder branch of the patient state generator network.

17. The method of claim 16, wherein the 3D spatial transform is a deformation vector field (DVF).

18. The method of claim 16, wherein the real-time stream of images is a stream of slices of magnetic resonance (MR) images or a kV projection image (X-ray).

19. The method of claim 16, wherein the 3D reference volume is a 3D magnetic resonance (MR) image or a 3D computed tomography (CT) image.

20. The method of claim 16, wherein the patient state generator network is trained as a single neural network.

* * * * *